(12) United States Patent
Lamoureux et al.

(10) Patent No.: US 7,874,976 B1
(45) Date of Patent: Jan. 25, 2011

(54) ECHOGENIC STRANDS AND SPACERS THEREIN

(75) Inventors: Gary A. Lamoureux, Woodbury, CT (US); Richard A. Terwilliger, Livingston, TX (US)

(73) Assignee: Biocompatibles UK Limited, Farnham, Surrey (GB)

(*) Notice: Subject to any disclaimer, the term of this patent is extended or adjusted under 35 U.S.C. 154(b) by 1076 days.

(21) Appl. No.: 11/517,649

(22) Filed: Sep. 7, 2006

(51) Int. Cl.
*A61M 36/00* (2006.01)

(52) U.S. Cl. .................................. 600/7; 600/8

(58) Field of Classification Search ............. 600/1–8
See application file for complete search history.

(56) References Cited

U.S. PATENT DOCUMENTS

| | | |
|---|---|---|
| 1,578,945 A | 3/1926 | Withers |
| 2,067,589 A | 1/1937 | Antrim |
| 2,153,889 A | 4/1939 | Frederick |
| 2,575,138 A | 11/1951 | Slaughter |
| 2,668,162 A | 2/1954 | Lowe |
| 2,703,316 A | 3/1955 | Schneider |
| 2,758,987 A | 8/1956 | Salzberg |
| 3,187,752 A | 6/1965 | Glick |
| 3,297,033 A | 1/1967 | Schmitt et al. |
| 3,351,049 A | 11/1967 | Lawrence |
| 3,565,869 A | 2/1971 | De Prospero |
| 3,636,956 A | 1/1972 | Schneider |
| 3,752,630 A | 8/1973 | Takagi |
| 3,811,426 A | 5/1974 | Culver et al. |
| 3,839,297 A | 10/1974 | Wasserman et al. |
| 3,936,414 A | 2/1976 | Wright et al. |
| 4,052,988 A | 10/1977 | Doddi |
| 4,086,914 A | 5/1978 | Moore |
| 4,141,087 A | 2/1979 | Shalaby et al. |
| 4,167,179 A | 9/1979 | Kirsch |
| 4,402,308 A | 9/1983 | Scott |
| 4,416,308 A | 11/1983 | Simpson et al. |
| 4,416,659 A | 11/1983 | Simpson et al. |
| 4,441,496 A | 4/1984 | Shalaby et al. |
| 4,452,973 A | 6/1984 | Casey et al. |
| 4,473,670 A | 9/1984 | Kessidis |

(Continued)

FOREIGN PATENT DOCUMENTS

EP 0 030 822 B1 9/1983

(Continued)

OTHER PUBLICATIONS

Amersham Health; "OncoSeed Indications"; http://www.amershamhealth-us.com/oncoseed/; printed Nov. 19, 2003.

(Continued)

*Primary Examiner*—Charles A Marmor, II
*Assistant Examiner*—Carrie Dorna
(74) *Attorney, Agent, or Firm*—Fliesler Meyer LLP

(57) ABSTRACT

Echogenic strands and spacers are provided for use in brachytherapy. Methods of making the strands and spacers are also provided. An echogenic strand for use in brachytherapy includes an encapsulating material, a seed disposed within the encapsulating material, and a spacer disposed within the encapsulating material and arranged adjacent to the seed. The spacer has an external length and a chamber formed along the external length, the chamber being adapted to improve ultrasound visibility relative to the spacer.

12 Claims, 3 Drawing Sheets

U.S. PATENT DOCUMENTS

| | | |
|---|---|---|
| 4,509,506 A | 4/1985 | Windorski et al. |
| 4,510,295 A | 4/1985 | Bezwada |
| 4,612,923 A | 9/1986 | Kronenthal |
| 4,646,741 A | 3/1987 | Smith |
| 4,689,424 A | 8/1987 | Shalaby et al. |
| 4,697,575 A | 10/1987 | Horowitz |
| 4,702,228 A | 10/1987 | Russell et al. |
| 4,741,337 A | 5/1988 | Smith |
| 4,754,745 A | 7/1988 | Horowitz |
| 4,772,287 A | 9/1988 | Ray et al. |
| 4,784,116 A | 11/1988 | Russell, Jr. et al. |
| 4,815,449 A | 3/1989 | Horowitz |
| 4,847,505 A | 7/1989 | Suthanthiran |
| 4,891,165 A | 1/1990 | Suthanthiran |
| 4,916,209 A | 4/1990 | Fung et al. |
| 4,936,823 A | 6/1990 | Colvin et al. |
| 4,946,435 A | 8/1990 | Suthanthiran et al. |
| 5,022,940 A | 6/1991 | Mehoudar |
| 5,242,373 A | 9/1993 | Scott et al. |
| 5,264,540 A | 11/1993 | Cooper et al. |
| 5,339,812 A | 8/1994 | Hardy et al. |
| 5,391,139 A | 2/1995 | Edmundson |
| 5,397,816 A | 3/1995 | Reilley et al. |
| 5,403,576 A | 4/1995 | Lin et al. |
| 5,405,309 A | 4/1995 | Carden, Jr. |
| 5,460,592 A | 10/1995 | Langton et al. |
| 5,521,280 A | 5/1996 | Reilly et al. |
| 5,713,828 A | 2/1998 | Coniglione |
| 5,755,704 A | 5/1998 | Lunn |
| 5,761,877 A | 6/1998 | Quandt |
| 5,833,593 A | 11/1998 | Liprie |
| 5,860,909 A | 1/1999 | Mick et al. |
| 5,928,130 A | 7/1999 | Schmidt |
| 5,938,583 A | 8/1999 | Grimm |
| 6,007,475 A | 12/1999 | Slater et al. |
| 6,010,446 A | 1/2000 | Grimm |
| 6,039,684 A | 3/2000 | Ildstad et al. |
| 6,053,858 A | 4/2000 | Bueche et al. |
| 6,080,099 A | 6/2000 | Slater et al. |
| 6,086,942 A | 7/2000 | Carden et al. |
| 6,099,457 A | 8/2000 | Good |
| 6,132,359 A | 10/2000 | Bolenbaugh |
| 6,132,677 A | 10/2000 | Ohriner |
| 6,132,947 A | 10/2000 | Honan et al. |
| 6,159,143 A | 12/2000 | Lennox |
| 6,163,947 A | 12/2000 | Coniglione |
| 6,200,255 B1 | 3/2001 | Yu |
| 6,200,256 B1 | 3/2001 | Weinberger |
| 6,200,258 B1 | 3/2001 | Slater et al. |
| 6,213,932 B1 | 4/2001 | Schmidt |
| 6,248,057 B1 | 6/2001 | Mavity et al. |
| 6,264,599 B1 | 7/2001 | Slater et al. |
| 6,264,600 B1 | 7/2001 | Grimm |
| 6,273,851 B1 | 8/2001 | Slater et al. |
| 6,283,911 B1 | 9/2001 | Keren |
| 6,312,374 B1 | 11/2001 | von Hoffmann |
| 6,319,190 B1 | 11/2001 | Schmidt et al. |
| 6,327,490 B1 | 12/2001 | Spetz |
| 6,358,195 B1 | 3/2002 | Green et al. |
| 6,360,116 B1 | 3/2002 | Jackson, Jr. et al. |
| 6,387,034 B1 | 5/2002 | Lee |
| 6,398,709 B1 | 6/2002 | Ehr et al. |
| 6,403,916 B1 | 6/2002 | Spooner et al. |
| 6,419,621 B1 | 7/2002 | Sioshansi et al. |
| 6,428,504 B1 | 8/2002 | Riaziat et al. |
| 6,436,026 B1 | 8/2002 | Sioshansi et al. |
| 6,438,401 B1 | 8/2002 | Cheng et al. |
| 6,450,937 B1 | 9/2002 | Mercereau et al. |
| 6,450,938 B1 | 9/2002 | Miller |
| 6,450,939 B1 | 9/2002 | Grimm |
| 6,471,631 B1 | 10/2002 | Slater et al. |
| 6,472,675 B2 | 10/2002 | White et al. |
| 6,474,535 B1 | 11/2002 | Shanks et al. |
| 6,482,178 B1 | 11/2002 | Andrews et al. |
| 6,497,646 B1 | 12/2002 | Candelaria et al. |
| 6,500,109 B2 | 12/2002 | Tokita et al. |
| 6,514,193 B2 | 2/2003 | Kaplan |
| 6,537,192 B1 | 3/2003 | Elliott et al. |
| 6,537,193 B1 | 3/2003 | Lennox |
| 6,539,247 B2 | 3/2003 | Spetz |
| 6,549,802 B2 | 4/2003 | Thornton |
| 6,554,760 B2 | 4/2003 | Lamoureux et al. |
| 6,561,967 B2 | 5/2003 | Schmidt |
| 6,569,076 B1 * | 5/2003 | Larsen et al. ............... 600/3 |
| 6,572,525 B1 | 6/2003 | Yoshizumi |
| 6,572,527 B2 | 6/2003 | Steele, Sr. et al. |
| 6,575,888 B2 | 6/2003 | Zamora et al. |
| 6,585,633 B2 | 7/2003 | Vitali et al. |
| 6,595,908 B2 | 7/2003 | Loffler et al. |
| 6,599,231 B1 | 7/2003 | Elliot et al. |
| 6,612,976 B2 | 9/2003 | Rosenthal et al. |
| 6,616,593 B1 | 9/2003 | Elliot et al. |
| 6,616,594 B2 | 9/2003 | Fontayne et al. |
| 6,626,817 B2 | 9/2003 | Luth |
| 6,632,176 B2 | 10/2003 | McIntire et al. |
| 6,638,205 B1 | 10/2003 | Chan et al. |
| 6,638,206 B2 | 10/2003 | Green et al. |
| 6,639,237 B2 | 10/2003 | Pedersen et al. |
| 6,648,811 B2 | 11/2003 | Sierocuk et al. |
| 6,656,106 B2 | 12/2003 | Schmidt |
| 6,656,107 B1 | 12/2003 | Pedersen et al. |
| 6,669,621 B2 | 12/2003 | O'Hara et al. |
| 6,669,622 B2 | 12/2003 | Reed et al. |
| 6,679,824 B1 | 1/2004 | Reed et al. |
| 6,682,471 B2 | 1/2004 | Steele, Sr. et al. |
| 6,689,043 B1 | 2/2004 | McIntire et al. |
| 6,709,381 B2 | 3/2004 | Munro, III |
| 6,716,156 B2 | 4/2004 | Menuhr et al. |
| 6,723,037 B2 | 4/2004 | Hamazaki et al. |
| 6,726,617 B1 | 4/2004 | Schmidt |
| 6,746,661 B2 | 6/2004 | Kaplan |
| 6,749,554 B1 | 6/2004 | Snow et al. |
| 6,752,753 B1 | 6/2004 | Hoskins et al. |
| 6,755,775 B2 | 6/2004 | Kalas et al. |
| 6,761,680 B2 | 7/2004 | Terwilliger et al. |
| 6,786,858 B2 | 9/2004 | Terwilliger et al. |
| 6,790,170 B2 | 9/2004 | Moody et al. |
| 6,800,055 B2 | 10/2004 | Amols et al. |
| 6,805,898 B1 | 10/2004 | Wu et al. |
| 6,820,318 B2 | 11/2004 | Terwilliger et al. |
| 6,837,844 B1 | 1/2005 | Ellard et al. |
| 6,846,283 B2 | 1/2005 | Green et al. |
| 6,905,455 B2 | 6/2005 | Rapach et al. |
| 6,911,000 B2 | 6/2005 | Mick et al. |
| 6,926,657 B1 | 8/2005 | Reed et al. |
| 6,969,344 B2 | 11/2005 | Drobnik et al. |
| 6,989,543 B2 | 1/2006 | Drobnik et al. |
| 7,008,367 B2 | 3/2006 | Visscher et al. |
| 7,060,020 B2 | 6/2006 | Terwilliger et al. |
| 7,074,291 B2 | 7/2006 | Terwilliger et al. |
| 7,083,566 B2 | 8/2006 | Tornes et al. |
| 7,094,198 B2 | 8/2006 | Terwilliger et al. |
| 7,118,523 B2 | 10/2006 | Loffler et al. |
| 7,211,039 B2 | 5/2007 | Lamoureux et al. |
| 7,267,643 B2 | 9/2007 | Koster et al. |
| 7,322,928 B2 | 1/2008 | Reed et al. |
| 7,497,818 B2 | 3/2009 | Terwilliger et al. |
| 7,601,113 B2 | 10/2009 | Lebovic et al. |
| 2001/0047185 A1 | 11/2001 | Satz |
| 2002/0066824 A1 | 6/2002 | Floyd et al. |
| 2002/0188195 A1 * | 12/2002 | Mills ..................... 600/431 |
| 2003/0084988 A1 | 5/2003 | Terwilliger et al. |
| 2003/0088144 A1 * | 5/2003 | Terwilliger et al. ............ 600/8 |
| 2003/0092958 A1 | 5/2003 | Terwilliger et al. |

| 2003/0181794 | A1 | 9/2003 | Rini et al. |
| 2003/0191355 | A1 | 10/2003 | Ferguson |
| 2004/0024453 | A1 | 2/2004 | Castillejos |
| 2004/0109823 | A1 | 6/2004 | Kaplan |
| 2004/0158117 | A1 | 8/2004 | Drobnik et al. |
| 2004/0158118 | A1 | 8/2004 | Drobnik et al. |
| 2004/0225174 | A1 | 11/2004 | Fuller et al. |
| 2005/0049490 | A1 | 3/2005 | Mills |
| 2005/0261541 | A1 | 11/2005 | Henderson et al. |
| 2006/0052654 | A1 | 3/2006 | Drobnik et al. |
| 2006/0063960 | A1 | 3/2006 | Wissman et al. |
| 2006/0094983 | A1 | 5/2006 | Burbank et al. |
| 2006/0121080 | A1 | 6/2006 | Lye et al. |
| 2006/0177379 | A1 | 8/2006 | Asgari |
| 2007/0224234 | A1 | 9/2007 | Steckel et al. |
| 2007/0238983 | A1 | 10/2007 | Suthanthiran |

FOREIGN PATENT DOCUMENTS

| EP | 0 292 630 A | 11/1988 |
| EP | 0 466 681 B1 | 1/1992 |
| EP | 0 668 088 A | 8/1995 |
| EP | 0993 843 A | 4/2000 |
| EP | 1 240 920 A | 9/2002 |
| WO | WO 00/64538 | 2/2000 |
| WO | WO 00/61229 | 10/2000 |
| WO | WO 2008/106586 | 9/2008 |

OTHER PUBLICATIONS

Merrick et al., "Seed Fixity in the Prostate/Periprostatic Region Following Brachytherapy," IJROBP, vol. 46(1): pp. 215-220 (2000).

Poggi et al., "Marker Seed Migration in Prostate Localization," IJROBP, vol. 56(5): pp. 1248-1251 (2003).

Tapen et al., "Reduction of Radioactive Seed Embolization to the Lung Following Prostate Brachtherapy," IJROBP, vol. 42(5): pp. 1063-1067 (1998).

Meiller R., "Advances May Improve Prostate Cancer Treatment," Board of Regents of the University of Wisconsin System; <http://www.news.wisc.edu/11899.html>, 3 pages (Dec. 1, 2005).

Alvaro Martinez, et al; "Sterilization of $^{125}$I Seeds Encased in Vicryl Sutures for Permanent Interstitial Implantation"; Intl. J. Radiation Oncology Biol. Phys. vol. 5, pp. 411-413; Pergamen Press Ltd., 1979.

Van't Riet, "Ultrasonically Guided Transperineal Seed Implantation of the Prostate: Modification of the Technique and Qualitative Assessment of Implants", Intl. J. Rad. Onc. Biol. Phys. 24(3): 555-558 (1992).

Middleton et al., "Synthetic Biodegradable Polymers as Medical Devices", Med. Plas. Biomat. (Mar. 1998).

http://investor.mentorcorp.com/news/20010122-32414.cfm, "Mentor Acquires Breakthrough Brachytherapy Technology" (Jan. 25, 2002).

Webster's II New Riverside University Dictionary, p. 191, 1984.

Medi-Physics brochure entitled I-125 Seeds. No. 6711, Medi-Physics, Inc. Arlington Heights Il. 60004, USA; Revised. Oct. 1999, 2 pages.

Medi-Physics brochure entitled I-125 Seeds. No. 7000; Medi-Physics, Inc. Arlington Heights Il. 60004, USA; Revised. Oct. 1999, 2 pages.

Amersham Health; "EchoSeed™"; http://www.amershamhealth-us.com/echoseed/ printed Nov. 19, 2003.

Amersham Health; "Rapid Strand Indications" Http;//www.amershamhealth-us.com/products/index.htp?a=i&i=38; printed Nov. 19, 2003.

Amersham Health; OncoSeed™ (Iodine-125 Seeds) http://www.amershamhealty-us.com/oncoseed/; print Nov. 19, 2003.

RadioMed: Innovative Products for Radiation, "The Visicoil Advantage . . . for Image Guided Radiation Therapy," http://www.radiomed.com/visicoil/, at lease as early as Aug. 2003.

Oncura, "RapidStrandR$_x$: The Logical Choice for Improved Dosimetry," Ocura Inc., Plymouth Meeting, PA, Apr. 2005.

* cited by examiner

ECHOGENIC STRANDS AND SPACERS THEREIN

FIELD OF THE INVENTION

This invention relates to radiotherapy. More particularly, it relates to strands for use in brachytherapy, and to spacers that are used to space radioactive seeds within such strands, while increasing the ultrasound visibility of the strands.

BACKGROUND

In interstitial radiation therapy, a tumor can be treated by temporarily or permanently placing small, radioactive seeds into or adjacent the tumor site. This can be accomplished by implanting loose seeds in the target tissue, or by implanting in the target tissue seeds that are connected to one another by a bio-absorbable material.

To implant loose seeds, an applicator device (e.g., a MICK® applicator or the like) that includes a needle is often used. A stylet is initially fully extended through a bore in the needle and the needle is inserted into a patient in an area where a row of loose seeds are to be implanted. The stylet is then retracted from the needle, enabling a loose seed from a magazine to enter the bore of the needle. The stylet is then pushed against the loose seed, forcing the seed through the bore of needle and into the target tissue. After a first seed has been implanted, the needle is withdrawn from the patient's body by a particular distance so that a next seed to be implanted is spaced apart from the first seed. Then, the stylet is again retracted to enable the next seed from the magazine to be positioned for movement into the needle. The stylet is then advanced through the needle to force the next seed into the target tissue at a desired distance away from the first seed. This procedure is repeated for subsequent seed implants. Additional details of this implantation technique and the applicator used to perform this technique can be found in U.S. Pat. No. 5,860,909, which is incorporated herein by reference.

In the above technique, loose seeds are deposited in a track made by the needle. However, when the needle is withdrawn, there is a tendency for the seeds to migrate in that track resulting in improper distribution of the seeds. Additionally, after implantation, the loose seeds are dependent on the tissue itself to hold each individual seed in place. This may result in the loose seeds migrating over time away from the initial site of implantation. Such migration of seeds is undesirable from a clinical perspective, as this may lead to underdosing or overdosing of a tumor or other diseased tissue and/or exposure of healthy tissue to radiation. The loose seeds may also rotate or twist from the original orientation at which the seeds were implanted. This is also undesirable from a clinical perspective, because the radiation pattern of the seeds may be directional, thereby causing underdosing or overdosing of a tumor or other diseased tissue and/or exposure of healthy tissue to radiation. Further complicating the implantation of loose seeds is the fact that the seeds are small, because they need to fit in small bore needles to prevent excessive tissue damage. Due to their small size and high seed surface dose, the seeds are difficult to handle and to label, and can easily be lost. In addition, the above described technique for implantation of individual loose seeds is time consuming.

Because of the disadvantages of using loose seeds, many physicians prefer using elongated members (often referred to as strands) that contains multiple seeds spaced from one another at desired increments. Such strands are capable of being loaded into an introducer needle just prior to the implant procedure, or they may be pre-loaded into a needle. Implantation of strands is less time consuming than implanting loose seeds. Additionally, because the seeds in the strands are connected to one another by a bio-absorbable material, there is less of a tendency for the seeds to migrate and/or rotate after implantation.

There are numerous techniques for making strands that include multiple seeds. For example, such strands can be made using a bio-absorbable material, with the seeds and rigid teflon spacers between the seeds inserted into the material. Needles loaded with the seeds in the carrier bio-absorbable material are sterilized or autoclaved causing contraction of the carrier material and resulting in a rigid column of seeds and spacers. This technique was reported in "Ultrasonically Guided Transperineal Seed Implantation of the Prostate: Modification of the Technique and Qualitative Assessment of Implants" by Van't Riet, et al., International Journal of Radiation Oncology, Biology and Physics, Vol. 24, No. 3, pp. 555-558, 1992, which is incorporated herein by reference. Such rigid implants have many drawbacks, including not having the ability to flex with the tissue over the time that the bio-absorbable material dissolves. More specifically, as the tissue or glands shrink back to pre-operative size, and thus as the tissue recedes, a rigid elongated implant does not move with the tissue, but remain stationary relative to the patient. The final locations of the seeds relative to the tumor are thus not maintained and the dosage of the radioactive seeds does not meet the preoperative therapy plan. Accordingly, there is a desire to provide a strand of seeds that is capable of moving with tissue or glands as they shrink back to pre-operative size, thereby enabling the seeds to meet a preoperative therapy plan.

In another technique, disclosed in U.S. Pat. No. 5,460,592, which is incorporated herein by reference, seeds are held in a woven or braided bio-absorbable carrier such as a braided suture. The carrier with the seeds laced therein is then secured in place to form a suitable implant. This braided assembly exhibits many drawbacks, as and when the braided assembly is placed into the target tissue. The needle that carries the braided strand assembly must be blocked at the distal end to prevent body fluids from entering the lumen. If body fluid reaches the braided strand assembly while the assembly is still in the lumen of the needle, the braided assembly can swell and jam in the lumen. Because the assembly is made of a braided tubular material, it is difficult to push the assembly out of the needle. As the needle is withdrawn from the tumor, pressure on the proximal end of the braided strand assembly causes the braid to expand and jam inside the lumen of the needle. Finally, if the braided strand is successfully expelled from the needle, the relative spacing of the seeds may not be maintained, if the braided material has collapsed. Accordingly, there is also a desire to provide a strand of seeds that can be implanted without causing jamming of a needle, and that after implantation the strand maintain the desired spacing of the seeds.

It is also desirable for a strand of seeds to be echogenic, i.e., be visible using ultrasound imaging, so that the implant can be visualized during implantation and during post operative visits to a physician. Techniques have been developed for making the seeds themselves more echogenic. For example, U.S. Pat. No. 6,632,176 suggests that seeds can be roughened, shaped or otherwise treated to improve the ultrasound visibility of the seeds. However, it is desirable that an entire strand be visible, not just the seeds therein. It has been suggested that the particles of materials such as glass, silica, sand, clay, etc. be mixed in with the bio-absorbable material to make the strand assembly of seeds more visible to ultrasound. However, the additions of such particles may effect the integrity of the strand. Additionally, such particles may irritate tissue after the bio-absorbable material has been absorbed. Further, it may be desirable to simply minimize the volume of materials that are not going to be absorbed by the body. Also, because it may be difficult to control the distribution of such particle, strand including such particles may not be uniformly visible by ultrasound.

Another technique that has been suggested to increase the ultrasound visibility of a strand of seeds is to introduce air bubbles into the bio-absorbable material during the manufacture of the strand, since air is a strong reflector of ultrasound energy having an inherent impedance many times greater than body tissue. This can be accomplished during the cooling stage of a molding process used to produce the strand, as disclosed in U.S. patent application Ser. No. 10/035,083, filed May 8, 2003, which is incorporated herein by reference. More specifically, during the cooling stage, the mold is placed in a vacuum chamber and the air in the chamber is evacuated. This causes the entrapped air in the mold to come out of solution from the polymer, and as the mold cools, this air is entrapped within the cooling polymer in the form of minute bubbles suspended in the plastic. A potential problem with this technique, however, is the inability to control the placement and size of the air bubbles. Thus, a strand including such air bubbles may not be uniformly visible by ultrasound. Accordingly, there is also a desire to improve the ultrasound visibility of a strand of seeds.

DETAILED DESCRIPTION

Embodiments of the present invention relate to spacers that can be used to space seeds from one another at desired increments within an elongated member (often referred to as a strand) that is used for interstitial radiation therapy. Embodiments of the present invention also relate to an elongated member (i.e., a strand) that includes such spacers. Additionally, embodiments of the present invention also relate to methods of making such spacers, and to methods of making an elongated member with such spacers. Strands, seeds, and echogenic spacers may be referred to herein generally or specifically as implants; however, an implant can include strands, seeds, echogenic spacers, and any other objected implantable at a surgical site. Implants are not intended to be limited to those structures described with specificity in the description below.

Figure 1A:
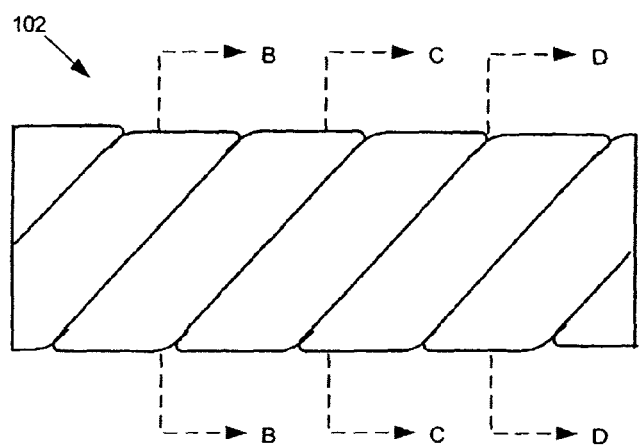
FIG. 1A is a side view of a spacer, according to an embodiment of the present invention.
Figure 1B:
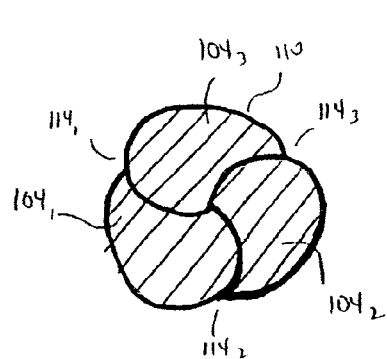
FIGS. 1B, 1C and 1D are, respectively, cross-sectional slices of the spacer shown in FIG. 1A, along lines B-B, C-C and D-D.
Figure 1C:
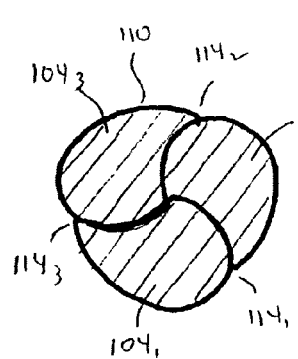
Figure 1D:
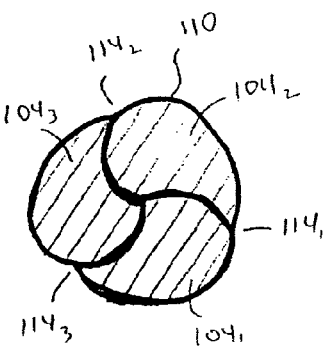

FIG. 1A shows a side view of a spacer 102, according to an embodiment of the present invention. Three cross sectional slices of the spacer 102 are shown in FIGS. 1B, 1C and 1D. As can be seen from the cross sectional slices, the spacer 102 is made up of three strings $104_1$, $104_2$ and $104_3$ that are twisted together to form an outer circumferential surface 110 that includes three helical grooves $114_1$, $114_2$ and $114_3$, with each of the grooves being formed where the strings $104_1$, $104_2$ and $104_3$ meet one another.

In accordance with an embodiment of the present invention, the strings $104_1$, $104_2$ and $104_3$ are made of a polymeric bio-absorbable material. In one specific embodiment, the strings $104_1$, $104_2$ and $104_3$ are lengths of suture material that can be purchased from Ethicon, Inc., of Somerville, N.J., under the trademark MONOCRYL® (polyglycoprone 25). A list of other possible materials for the strings $104_1$, $104_2$ and $104_3$ are provided below. The diameter of each string is, for example, between 0.005 and 0.020 inches, with a preferably diameter of about 0.012 inches. However, other diameters are possible.

In accordance with an embodiment of the present invention, the spacer 102 is manufactured by twisting the three strings $104_1$, $104_2$ and $104_3$ together as shown, placing the twisted strings in a hollow glass tube, heating the glass tube, and then cooling the glass tube, such that the strings $104_1$, $104_2$ and $104_3$ thermal set in the twisted configuration. The three twisted strings are then pulled out of the glass tube, leaving a structure that is made up of three twisted strings of polymeric bio-absorbable material, having the triple helix outer surface 110. The structure is then cut to appropriate sizes, to produce spacers. Like a tightly wound spring, such spacers will be generally axially rigid and radially flexible. Accordingly, a strand that is made using such spacers should be generally axially rigid and radially flexible, which is desirable.

In one embodiment, each string $104_1$, $104_2$ and $104_3$ has an initial diameter of about 0.012 inches. The strings $104_1$, $104_2$ and $104_3$ are twisted together to achieve a desired pitch, and then placed in a hollow glass tube. The glass tube can then be placed in an oven or otherwise exposed to heat, to thereby heat the strings $104_1$, $104_2$ and $104_3$. Preferably, the twisted strings $104_1$, $104_2$ and $104_3$ are placed in the oven while the oven is at least 100 degrees F. lower than the desired temperature to which the strands will be exposed. This desired temperature, which is dependent on the material from which the strings $104_1$, $104_2$ and $104_3$ are made, is a temperature at which the strings $104_1$, $104_2$ and $104_3$ will shrink, but not melt. For example, if the strings $104_1$, $104_2$ and $104_3$ are made from MONOCRYL® (polyglycoprone 25), then the strings $104_1$, $104_2$ and $104_3$ should be placed in an oven when the oven is less than 360 degrees F., and then the oven should be raised to a temperature of about 460 degrees F.

The glass tube, with the twisted strings $104_1$, $104_2$ and $104_3$ therein, is then cooled. Once cooled, the strings $104_1$, $104_2$ and $104_3$ are thermo set in their tightly wound configuration. At that point, the strings $104_1$, $104_2$ and $104_3$ are pulled out of the glass tube, thereby leaving an elongated structure that is made up of tightly wound strings $104_1$, $104_2$ and $104_3$, having an outer surface 110 that has helical grooves, and in this specific implementation a triple helix of grooves. This elongated structure is then cut into desired lengths to form spacers, which are used to space radioactive seeds from one another within an elongated therapeutic member known as a strand. The use of these spacers within a strand will be described in more detail below.

The outer diameter of the spacer 102 will be dependent on the diameter of each string $104_1$, $104_2$ and $104_3$, and the inner diameter of the hollow glass tube within which the twisted strings $104_1$, $104_2$ and $104_3$ are inserted and thermal set therein, and the amount by which the strings shrink during the thermal setting process. Assuming the diameter of each string $104_1$, $104_2$ and $104_3$ is about 0.012 inches, and the inner diameter of the hollow glass tube is about 0.025 inches, then the outer diameter of the spacer 102 will be about 0.024 inches.

As mentioned above, the spacers 102 of the present invention can be used to increase ultrasound visibility of a strand used in brachytherapy. More specifically, such a strand typically includes a plurality of radioactive seeds that are spaced apart from one another at desired intervals. These intervals can be selected to be any distance or combination of distances that are optimal for the treatment plan of a patient. The strand is preferably axially flexible such that it can be bent back upon itself without kinking However, the strand preferably has sufficient column strength along its longitudinal axis so that the strand can be urged out of a hollow needle without the strand folding upon itself The spacers 102 of the present invention can be used to maintain the desired spacings between seeds within the strand, when the strand is being made, while allowing the stand to be axially rigid and radially flexible. This will be better understood from the following discussion of how such strands can be made.

Figure 2A:
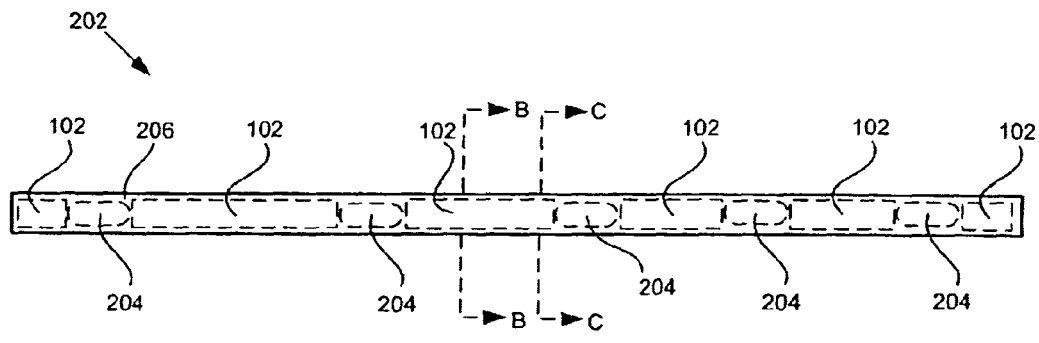
FIG. 2A illustrates a side view of a strand for use in brachytherapy that includes spacers of the present invention.

A side view of an exemplary strand 202, according to an embodiment of the present invention, is shown in FIG. 2A. The strand 202 includes a plurality of radioactive seeds 204 that are spaced apart from one another at desired intervals using spacers 102 of the present invention. Encapsulating the spacers 102 and the seeds 204 is a material 206. The material can be formed as a hollow tube or VICRYL® "sock" where the seeds and elements are pushed in. A list of other possible materials for the material 206 are provided below.

Figure 2B:
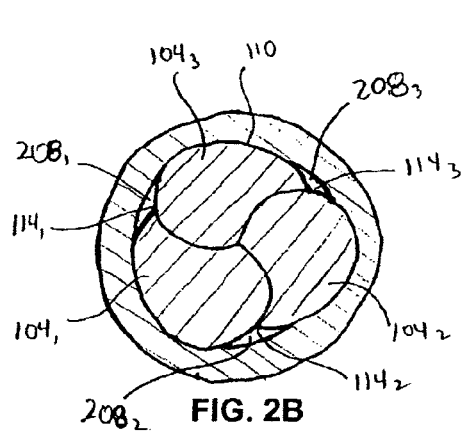
FIGS. 2B and 2C are, respectively, cross-sectional slices of the strand shown in FIG. 2A, along lines B-B and C-C.
Figure 2C:
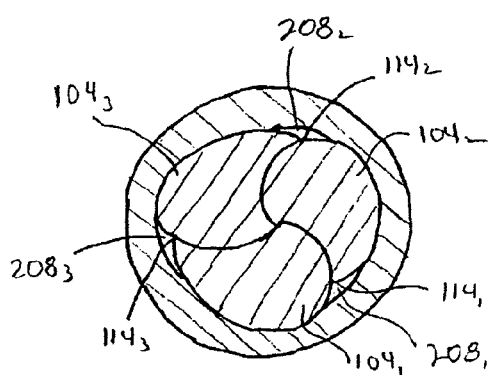

Two possible cross sectional slices of the strand 202 are shown in FIGS. 2B and 2C. After the spacers 102 are encapsulated within the material 206, hollow helical chambers $208_1$, $208_2$ and $208_3$ are formed adjacent to the outer surface 110 of the spacers 102. More specifically, the material 206 has a viscosity such that the helical grooves $114_1$, $114_2$ and $114_3$ on the outer surface 110 of the spacers 102 are not filled in by the material 206, so that each groove forms a respective hollow helical chamber $208_1$, $208_2$ and $208_3$ that extends in an axial direction with respect to the spacer 102 and strand 202. In the embodiment shown in FIGS. 2B and 2C, three hollow helical chambers $208_1$, $208_2$ and $208_3$ are formed (i.e., one chamber 208 for each groove 114), which, as will be described below, increase the ultrasound visibility of the strand 202.

The strand 202 can be manufacture in various manners. For example, the strand 202 can be manufactured using a hollow tube or VICRYL® "sock" by pushing the seeds and spacing elements into the tube or a molding processes, such as, but not limited to, compression molding or injection molding. In one example, the plurality of radioactive seeds 204 and the spacers 102 are inserted into the tube or "sock". The spacers 202 can be of the same length, or of different lengths, if the preoperative therapeutic plan so specifies. The spacers 202 can be made available in the plurality of different lengths, or the spacers can be cut to their proper lengths.

The encapsulating material 206 should be such that the encapsulating material should not fill the helical grooves $114_1$, $114_2$ and $114_3$ of the spacers 102, resulting in hollow helical chambers $208_1$, $208_2$ and $208_3$ surrounding the spacers 102.

Ultrasound visibility is highly dependent upon the angular orientation of a surface with respect to the ultrasound inducer that is used for imaging. Generally, a smooth surface will act as a mirror, scattering ultrasound waves in a numerous directions unless the angle between the sound and the surface is very close to 90 degrees. Accordingly, if surfaces of a spacer were relatively smooth, such surfaces would reflect ultrasound waves in a generally fan shaped conical pattern that spanned a large spatial angle, only giving a strong ultrasound reflections when imaged at an angle very close to 90 degrees. In contrast, in the present invention, because the hollow helical chambers $208_1$, $208_2$ and $208_3$ have helical surfaces, at least a portion of such surfaces will likely be substantially 90 degrees from incoming ultrasound waves. Accordingly, the spacers of the present invention avoid angular dependence of the reflected ultrasound.

As shown in FIG. 2, spacers 102 can also be placed near the distal ends of the strand 202, to thereby increase the ultrasound visibility of the ends of the strand 202.

Figure 3:
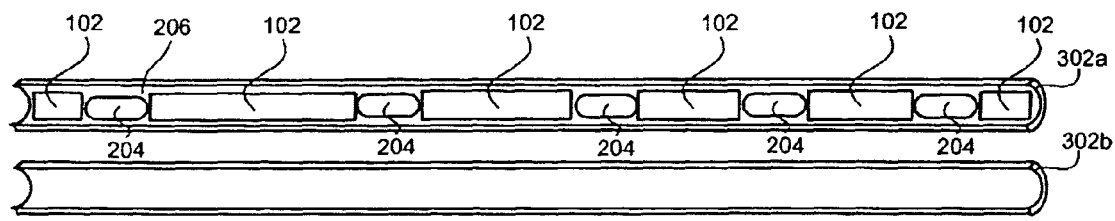
FIG. 3 illustrates a pair of half-shells within which radioactive seeds and spacers of the present invention can be placed to form an echogenic strand for use in brachytherapy.

Referring now to FIG. 3, in another embodiment a strand 202 can be constructed using a pair of pre-formed elongated members 302a and 302b of bio-absorbable material that are shaped like half-shells. Such half-shells 302a and 302b are described in additional detail in U.S. Pat. No. 6,761,680, which is incorporated herein by reference. The seeds 204 and spacers 102 are placed within one of half-shells 302a. The second half-shell 302b is then mated with the first half-shell 302a, and the half-shells 302a and 302b are heated, fusing the half-shells 302a and 302b together and fixing the seeds 204 and spacers 102 inside. The material of the half-shells 302a and 302b should have a lower melt temperature than the spacers 102, so that the half-shells can be fused without melting the spacers 102.

In another embodiments, a strand can be made by inserting (i.e., pushing) the seeds 204 and spacers 102 through an opening in one end of an elongated hollow tube of bio-absorbable material. Additional details of a seed pusher that can be used in this process are described in U.S. Pat. No. 6,761,680, which was incorporated herein by reference above.

In still another embodiment, a strand can be made by inserting the seeds 204 and spacers 102 into a tube of braided bio-absorbable material. Additional details of such a braided bio-absorbable tube are described in U.S. Pat. No. 5,460,592, which is incorporated herein by reference.

In each of the above described embodiments for manufacturing a strand 202 for use in brachytherapy, and encapsulating material 206 encapsulates the seeds 204 and spacers 102 within the strand 202. After the strand is manufactured, it can then be inserted into a patient for use in interstitial radiation therapy. An exemplary device that can be used to perform such insertion into a patient will now be described with reference to FIG. 4.

Figure 4:
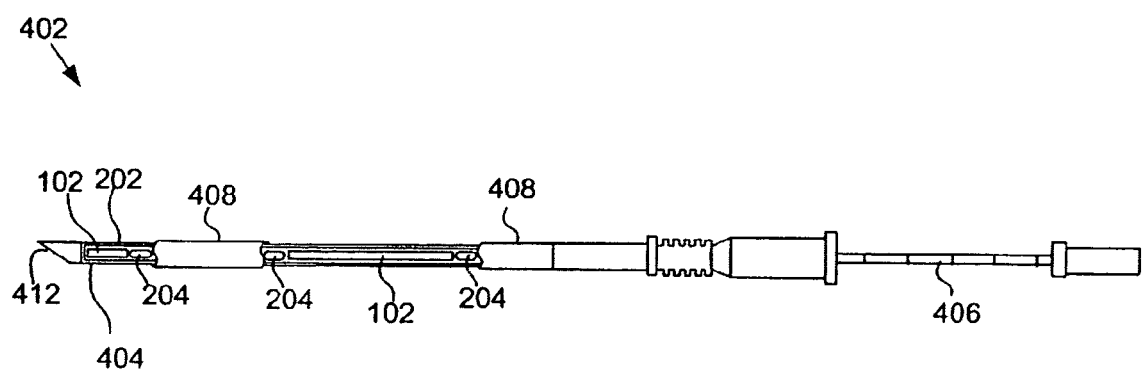
FIG. 4 illustrates an exemplary brachytherapy device that can be used to implant strands of the present invention into a patient.

FIG. 4 is a side view of a brachytherapy device 402, which includes a needle 404 and a stylet 406. The needle 404 is shown partially broken away and has a sheath component 408, and is loaded with a strand 202 of the present invention. A beveled end 412 of the needle 404 is plugged with a bio-compatible substance to prevent fluids and tissue from entering the needle 404 and coming in contact with the strand 202 prior to the placement of the strand 202 at its desired location (e.g., adjacent a tumor). The plug can be made out of a bone wax or can be made of one of the bio-absorbable polymers or copolymers listed below. In operation, the stylet 406 is inserted into the needle 404 until it meets the strand 202. Then the needle 404 is inserted into a patient at the desired site. The strand 202 is gradually extruded from the needle 404 via the static force of the stationary stylet 406, as the needle 404 is pulled back and removed from the patient.

In the embodiments described above, the spacers 102 were described as being made from three strings $104_1$, $104_2$ and $104_3$. While it is preferred that at least three strings $104_1$, $104_2$ and $104_3$ are used to produce the echogenic spacers of the present invention, it is also within the scope of the present invention that two strings be used. It is also within the scope of the present invention that more than three strings may be used to make a spacer. Regardless of the number of strings, spacers can be made by twisting the strings together and thermal setting the twisted string structure. Changing the number of strings used to make the spacer 102 will change the number of helical grooves, and thus the number of hollow helical chambers in a strand that is formed using the spacer 102.

It is preferable that the strings used to make spacers 102 and the encapsulating material 206 used to make strands 202 (with the spacer 102 and seeds 204 therein) are bio-absorbable.

Example types of materials that are bio-absorbable include, but are not limited to, synthetic polymers and copolymers of glycolide and lactide, polydioxanone and the like. Such polymeric materials are more fully described in U.S. Pat. Nos. 3,565,869, 3,636,956, 4,052,988 and European Patent Publication No. 0030822, all of which are incorporated herein by reference. Specific examples of bio-absorbable polymeric materials that can be used to produce embodiments of the present invention are polymers made by Ethicon, Inc., of Somerville, N.J., under the trademarks MONOCRYL® (polyglycoprone 25), MAXON® (Glycolide and Trimethylene Carbonate), VICRYL® (polyglactin 910, also known as PGA) and PDS II™ (polydioanone).

Other exemplary bio-absorbable materials include poly (glycolic acid) (PGA) and poly(-L-lactic acid) (PLLA), polyester amides of glycolic or lactic acids such as polymers and copolymers of glycolate and lactate, polydioxanone and the like, or combinations thereof. Such materials are more fully described in U.S. Pat. No. 5,460,592 which is hereby incorporated by reference. Further exemplary bio-absorbable polymers and polymer compositions that can be used in this invention are described in the following patents which are hereby incorporated by reference: U.S. Pat. No. 4,052,988 which discloses compositions comprising extruded and oriented filaments of polymers of p-dioxanone and 1,4-dioxepan-2-one; U.S. Pat. No. 3,839,297 which discloses compositions comprising poly[L(–)lactide-co-glycolide] suitable for use as absorbable sutures; U.S. Pat. No. 3,297,033 which discloses the use of compositions comprising polyglycolide homopolymers as absorbable sutures; U.S. Pat. No. 2,668,162 which discloses compositions comprising high molecular weight polymers of glycolide with lactide; U.S. Pat. No. 2,703,316 which discloses compositions comprising polymers of lactide and copolymers of lactide with glycolide; U.S. Pat. No. 2,758,987 which discloses compositions comprising optically active homopolymers of L(–) lactide i.e. poly L-Lactide; U.S. Pat. No. 3,636,956 which discloses compositions of copolymers of L(–) lactide and glycolide having utility as absorbable sutures; U.S. Pat. No. 4,141,087 which discloses synthetic absorbable crystalline isomorphic copolyoxylate polymers derived from mixtures of cyclic and linear diols; U.S. Pat. No. 4,441,496 which discloses copolymers of p-dioxanone and 2,5-morpholinediones; U.S. Pat. No. 4,452,973 which discloses poly(glycolic acid)/poly(oxyalkylene) ABA triblock copolymers; U.S. Pat. No. 4,510,295 which discloses polyesters of substituted benzoic acid, dihydric alcohols, and glycolide and/or lactide; U.S. Pat. No. 4,612,923 which discloses surgical devices fabricated from synthetic absorbable polymer containing absorbable glass filler; U.S. Pat. No. 4,646,741 which discloses a surgical fastener comprising a blend of copolymers of lactide, glycolide, and poly(p-dioxanone); U.S. Pat. No. 4,741,337 which discloses a surgical fastener made from a glycolide-rich blend of polymers; U.S. Pat. No. 4,916,209 which discloses bio-absorbable semi-crystalline depsipeptide polymers; U.S. Pat. No. 5,264,540 which discloses bio-absorbable aromatic polyanhydride polymers; and U.S. Pat. No. 4,689,424 which discloses radiation sterilizable absorbable polymers of dihydric alcohols. If desired, to further increase the mechanical stiffness of the molded embodiments of the present invention, bio-absorbable polymers and polymer compositions can include bio-absorbable fillers, such as those described in U.S. Pat. No. 4,473,670 (which is incorporated by reference) which discloses a composition of a bio-absorbable polymer and a filler comprising a poly(succinimide); and U.S. Pat. No. 5,521,280 (which is incorporated by reference) which discloses bio-absorbable polymers and a filler of finely divided sodium chloride or potassium chloride.

Where the materials are bio-absorbable, the bio-absorbable material should preferably be absorbed in living tissue in a period of time of from about 70 to about 120 days, but can be manufactured to be absorbed anywhere in a range from 1 week to 1 year, depending on the therapeutic plan for a specific patient. Preferably the bio-absorbable material is selected to absorb about when the half-life of the radioactive seeds is reached. The materials should also be bio-compatible, whether or not they are bio-absorbable.

The term polymer, as used herein, is also meant to include copolymers. Table 1 below provides examples of bio-absorbable polymers suitable for use in producing embodiments of the present invention, along with specific characteristics (e.g., melting points) of the various polymers. A further discussion of such bio-absorbable polymers can be found in an article by John C. Middleton and Arthur J. Tipton entitled "Synthetic Biodegradable Polymers as Medical Devices," published March 1998 in Medical Plastics and Bio-materials, which article is incorporated herein by reference.

TABLE 1

Biodegradable polymers, properties and degradation time

| POLYMER | MELTING POINT (° C.) | GLASS-TRANSITION TEMP (° C.) | MODULUS Gpa$^a$ | DEGRADATION TIME (MONTHS)$^b$ |
|---|---|---|---|---|
| PGA | 225-230 | 35-40 | 7.0 | 6 to 12 |
| LPLA | 173-178 | 60-65 | 2.7 | >24 |
| DLPLA | Amorphous | 55-60 | 1.9 | 12 to 16 |
| PCL | 58-63 | (−65)-(−60) | 0.4 | >24 |
| PDO | N/A | (−10)-0 | 1.5 | 6 to 12 |
| PGA-TMC | N/A | N/A | 2.4 | 6 to 12 |
| 85/15 DLPLG | Amorphous | 50-55 | 2.0 | 5 to 6 |
| 75/25 DLPLG | Amorphous | 50-55 | 2.0 | 4 to 5 |

TABLE 1-continued

| 65/35 DLPLG | Amorphous | 45-50 | 2.0 | 3 to 4 |
| 50/50 DLPLG | Amorphous | 45-50 | 2.0 | 1 to 2 |

[a]Tensile or flexural modulus.
[b]Time to complete mass loss. Rate also depends on part geometry.

The seeds 204 included in the strands 202 can be of various types having low energy and low half-life such as Iodine seeds, known as I-125 seeds, including a welded titanium capsule containing iodine 125 absorbed on a silver rod, or Palladium 103 seeds. Exemplary dimensions of a seed 102 are 0.18 inches in length and 0.0315 inches in diameter. Exemplary seeds are listed below in Table 2, but embodiments of the present invention should not be limited to the seeds listed therein.

TABLE 2

Seed Manufacturers and Common Types of Seeds

| MANUFACTURER | SEED NAME |
|---|---|
| IODINE [125] | |
| Amersham 6711 | ONCOSEED ® |
| Amersham 6733 | ECHOSEED ® |
| Amersham 7000 | RAPID STRAND ® |
| North American Scientific | IOGOLD ™ |
| Best Industries | BEST IODINE-125 ™ |
| Bebig | SYMMETRA ™ |
| Mills Biopharmaceuticals | PROSTASEED ™ |
| Syncor | PHARMASEED ™ |
| International Isotopes | ISOSTAR ™ |
| Implant Sciences | I-PLANT ™ |
| International Brachytherapy | INTERSOURCE-125 ® |
| IsoAid | ADVANTAGE I-125 ™ |
| Source Tech | STM1251 ™ |
| DRAXIMAGE, Inc. | BRACHYSEED ® |
| PALLADIUM [103] | |
| North American Scientific | PD GOLD ™ |
| Theragenics | THERASEED 200 ® |
| Best Industries | BEST PALLADIUM-103 ™ |
| International Brachytherapy | INTERSOURCE 103 ® |

Alternatively, seeds 204 can be manufactured using iridium 192, cesium 131, gold 198, yttrium 90 and/or phosphorus 32. Further radioactive isotopes used to manufacture seeds are not limited to these examples, but can include other sources of different types of radiation.

In addition it is to be understood that other types of seeds can be used. For example, seeds such as those described in U.S. Pat. No. 6,248,057, which is incorporated herein by reference, can be used with the present invention. These seeds include radiation delivery devices, drug delivery devices, and combinations of radiation and drug delivery devices in the form of beads, seeds, particles, rods, gels, and the like. These particular seeds are absorbable wherein the radiation member or drug delivery member is contained within, for example, absorbable polymers such as those listed below or in the above-referenced patent. In such seeds, the bio-absorbable structure can have a predefined persistence which is the same as or substantially longer than a half life of the radioactive member contained in the bio-absorbable structure. These above bio-absorbable seeds can be used in the same manner as the seeds described herein with respect to the invention.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. A strand for use in brachytherapy, comprising:
   encapsulating material;
   a seed disposed within the encapsulating material;
   a spacer formed by at least two strings twisted together, the spacer disposed within the encapsulating material and arranged adjacent to the seed;
   wherein a length of the spacer is defined by a length of the at least two strings twisted together;
   wherein the at least two strings of the spacer do not cover the seed; and
   at least one chamber formed along the length of the spacer, the at least one chamber adapted to improve ultrasound visibility relative to the spacer;
   wherein each of the at least one chamber is formed between the encapsulating material and a groove at an abutment of two of the at least two strings.

2. The strand of claim 1, wherein the chamber has a generally helical shape.

3. The strand of claim 1, wherein at least two chambers are formed between the spacer and the encapsulating material.

4. The strand of claim 1, wherein the chamber is adapted to house one of a gas and a liquid having an ultrasonic reflectivity greater than an ultrasonic reflectivity of the patient tissue.

5. The strand of claim 1, wherein the seed is a first seed; and further comprising:
   a second seed disposed within the encapsulating material such that the spacer is arranged between the first seed and the second seed; and
   the length of the spacer extends generally between the first seed and the second seed.

6. The strand of claim 1, wherein the encapsulating material includes an elongated hollow tube.

7. A strand for use in brachytherapy, comprising:
   encapsulating material;
   a first seed disposed within the encapsulating material;
   a second seed disposed within the encapsulating material;
   a spacer formed by at least two strings twisted together, the spacer disposed within the encapsulating material and arranged between the first seed and the second seed;
   wherein a length of the spacer that separates the first seed from the second seed is defined by a length of the at least two strings twisted together; and
   at least one chamber having a generally helical shape formed along at least a portion of the length of the spacer, the at least one chamber adapted to improve ultrasound visibility relative to the spacer;
   wherein each of the at least one chamber is formed between the encapsulating material and a groove at an abutment of two of the at least two strings.

8. The strand of claim 7, wherein at least two helical chambers are formed between the spacer and the encapsulating material.

9. The strand of claim 7, wherein:
the spacer includes three strings twisted together such that the spacer has a generally helical shape; and
three chambers are formed between the spacer and the encapsulating material.

10. The strand of claim 7, wherein the chamber is adapted to house one of a gas and a liquid having an ultrasonic reflectivity greater than an ultrasonic reflectivity of the patient tissue.

11. The strand of claim 7, wherein the at least two strings are formed of a polymeric material.

12. A strand for use in brachytherapy comprising:
a pair of treatment seeds;
a spacer adapted to separate the pair of treatment seeds from one another, the spacer including
three polymeric strings twisted together so that the spacer has an outer circumferential surface, wherein the three twisted together polymeric strings have an axial length adapted to substantially define a space between the pair of treatment seeds; and
three helical grooves, each helical groove being formed in the outer circumferential surface where two of the three polymeric strings abut and each helical groove extending along the length of the spacer; and
encapsulating material covering said seeds and said spacer such that said three helical grooves and said encapsulating material form three chambers that improve ultrasound visibility of the spacer.

* * * * *